United States Patent
Panasyuk

(10) Patent No.: US 8,241,673 B2
(45) Date of Patent: Aug. 14, 2012

(54) METHOD FOR PRODUCING BIOMATERIALS FROM BONE TISSUE AND MATERIAL USED FOR OSTEOPLASTY AND TISSUE ENGINEERING

(75) Inventor: Andrey Fedorovich Panasyuk, Moscow (RU)

(73) Assignees: Dmitry Alekseevich Savaschuk (RU); Andrey Fedorovich Panasyuk (RU)

( * ) Notice: Subject to any disclaimer, the term of this patent is extended or adjusted under 35 U.S.C. 154(b) by 1069 days.

(21) Appl. No.: 12/091,741

(22) PCT Filed: Oct. 27, 2005

(86) PCT No.: PCT/RU2005/000526
§ 371 (c)(1),
(2), (4) Date: Apr. 25, 2008

(87) PCT Pub. No.: WO2007/049988
PCT Pub. Date: May 3, 2007

(65) Prior Publication Data
US 2008/0262632 A1    Oct. 23, 2008

(51) Int. Cl.
*A61K 35/32* (2006.01)
*A61F 2/28* (2006.01)
(52) U.S. Cl. ..................... 424/549; 623/23.63
(58) Field of Classification Search ............. 424/549; 623/23.63
See application file for complete search history.

(56) References Cited

U.S. PATENT DOCUMENTS

| 4,394,370 | A |   | 7/1983 | Jefferies |
|---|---|---|---|---|
| 4,627,853 | A |   | 12/1986 | Campbell |
| 4,743,259 | A |   | 5/1988 | Bolander |
| 5,728,159 | A | * | 3/1998 | Stroever et al. ............. 623/23.5 |
| 6,576,015 | B2 | * | 6/2003 | Geistlich et al. ............ 623/16.11 |
| 2003/0171810 | A1 | * | 9/2003 | Steiner ....................... 623/13.14 |

FOREIGN PATENT DOCUMENTS

| FR | 2582517 A1 | 12/1986 |
|---|---|---|
| RU | 2104703 C1 | 2/1998 |
| RU | 2232585 C1 | 7/2004 |
| RU | 2242981 C1 | 12/2004 |
| WO | WO9844809 A1 | 10/1998 |

OTHER PUBLICATIONS

International Search Report in PCT/RU2005/000526, dated Jun. 1, 2006, corresponding to the present application.

* cited by examiner

*Primary Examiner* — Rosanne Kosson
(74) *Attorney, Agent, or Firm* — Bardmesser Law Group

(57) ABSTRACT

A method for obtaining of biomaterials for osteoplasty and tissue engineering cleans a bone of natural origin, which is sawn to plates with a thickness of 0.2 to 2.0 cm, washed twice in 0.1 M phosphate buffer at 65° C., pH 5.8-6.0, calculated as two volumetric parts of the buffer solution per one part of bone, digested in a solution of activated 0.1-0.4% papain at 65° C. for 24 hours. The plates are washed with 5 volumes of water at the temperature 40-80° C., treated with 0.4 N alkali solution at room temperature for 10-24 hours, washed with flowing water, dried, defatted in ethanol/chloroform mixtures in proportion of 1:2 and then in proportion of 2:1, decalcified in 0.4-1 N hydrochloric acid, treated with 1.5-3% hydrogen peroxide for 4 hours, washed with treated water, then washed with ethanol, dried at room temperature, packed and sterilized.

19 Claims, No Drawings

METHOD FOR PRODUCING BIOMATERIALS FROM BONE TISSUE AND MATERIAL USED FOR OSTEOPLASTY AND TISSUE ENGINEERING

CROSS-REFERENCE TO RELATED APPLICATIONS

This application is a 371 of international application number PCT/RU2005/000526, filed on Oct. 27, 2005.

BACKGROUND OF THE INVENTION

1. Field of the Invention

This invention covers the field of medicine, in particular, biochemistry and biomaterials extraction technology and is also used for manufacturing of biomaterials applied as a plastic material by the operative restoration of bone defects by destruction of bone tissue, cystectomy, oncotomy and also as a carrier of active substances and drugs, in plastic surgery by restoration of organ's or tissue's volume.

2. Description of the Related Art

A bone is a living tissue, in which a continuous reorganization process including a simultaneous destruction and restoration of the bone material. Old tissue is remodulated during a normal process and also by implantation of a foreign material, new tissue is formed in place of this. Equilibrium is permanently maintained between the quantity of a reformed bone and a newly developed bone. This process will go easier if the implanted material is close to a habitual bone in its structure.

That is why at present it is preferred to prepare the substitute material from tissues of a natural bone, which must be of animal origin by reasons of ethics and practice.

It is well-known that a partial demineralization promotes implantation of a bone graft. Hereupon various additional steps are taken, which are intended either for full deproteinization of the bone or for influencing the nature of proteins remaining bound in the bone base or for increase of this share of proteins.

As regards to methods used heretofore, in particular, the U.S. Pat. No. 4,394,370 can be given as an example, where it is proposed to form a spongy mass by the melting of a mixture consisting of a powder of the demineralized bone of human origin and a diluted collagenic powder with the help of glutaraldehydic binding providing a cross-link.

The U.S. Pat. No. 4,743,259 combines demineralization by hydrochloric acid with enrichment by proteins carried out on the first part of the demineralized bone with the help of proteins extracted from the second part with use of guanidine.

Furthermore, it is proposed in patent application FR No. 2582517 to process bone ends taken from animals, namely, from livestock by means of a partial demineralization and tanning with use of glutaraldehyde. Bone fragments to be implanted by a surgeon are cut out with necessary shaping from cattle's bones after a preliminary pretreatment including delipidization or defatting operation with the use of an organic solvent such as ethanol, demineralization with the use of calcium extraction means such as hydrochloric acid and an operation providing for tanning with glutaraldehyde and also various washing operations.

It is obvious from the description of the prior art patents given above that the mentioned tanning process favors the features of a treated bone, as it facilitates the cross-linkage of macromolecular chains. However, it has been recently detected that the treatment of glutaraldehydes does not result in a significant reduction of immunogenic features and, moreover, the engraftment of the implanted bone occurs in a desirable degree, as opposed to the theory suggested earlier. Furthermore, such chemical compounds like glutaraldehyde have a disadvantage in that they are biologically toxic.

A method for obtaining a material for osteoplasty from the bone tissue of natural origin including the subsequent removal of lipids from the natural bone tissue with use of an organic solution, selective extraction with the subsequent washing and lyophilization of the end product is known, characterized by the selective extraction carried out with the use of a urea solution for denaturation and removal of antigenic proteins with the maintaining of a non-denaturated collagen of type I in a natural form located in the initial mineral bone structure and the obtained structure is directed to washing and lyophilization (RU No. 2104703, A61K35/32, publ. Feb. 20, 1998).

Therefore, the removal of lipids is carried out with use of the organic solution containing 10 volumetric parts of chloroform/methanol or ethanol/dichloromethane mixture per 1 part of bone in proportion 2:3-1:3 accordingly. The demineralization of the bone tissue is carried out with the solution of the hydrochloric acid with molarity of 0.1-1.0 M after removal of lipids. The extraction with an ionic solvent is carried out before the selective extraction, in particular, with use of sodium chloride.

The selective extraction is conducted with a 2 to 10 M urea solution, preferably with a 5 to 8 M solution or aqueous urea solution containing 0.1-0.5 vol. of mercaptoethanol. The washing is carried out with use of distilled water at 30-60° C., preferably at 45-55° C. Alternatively, the selective extraction is carried out first with use of the urea solution in concentration from 2 to 10 M, preferably within the limits of 5 to 8 M, then, after washing, with use of the aqueous urea solution containing mercaptoethanol in quantity of 0.1 to 0.5 vol. in the solution.

The material for osteoplasty obtained by such a way represents a compound, in which the bone structure of natural origin containing 20-40% (namely 25-35%) of a non-denaturated collagen of type I is maintained. According to analysis results of dry material, this material contains less than 15% lipids, 25-45% proteins, 10-30% calcium, 5-20% phosphorus and has a water content below 10% and a Ca/P ratio in preference from 1 to 2.2.

The material can have a shape of parallelepipedic blocks, truncated pyramids, plates, discs or powder amalgamated with a binder which can preferably be of biological origin such as fibrin or synthetic origin such as, for example, synthetic biodegradable polymer.

This invention is chosen as a prototype both for the method and material, as it is the closest to the proposed invention as regards to its engineering solution.

The disadvantage of the mentioned method is the fact that such treatment, although it maintains a bone collagen of type 1 in the natural form, does not provide full removal of antigens such as non-collagenic proteins, lipids, lipoproteins and other substances reducing the biocompatibility of the obtained material from this tissue.

BRIEF SUMMARY OF THE INVENTION

The goal of the invention is to improve the quality of the biomaterial obtained containing hydroxyapatite and/or bone collagen from a bone tissue and to obtain materials for application in stomatology, traumatology and orthopedics on its basis by means of maintaining the native structure of the bone collagen and spatial organization of the bone tissue for its subsequent cellular colonization, engraftment capacity of such biomaterials at the expense of their antigenic features, to increase the biocompatibility and biointegration.

The technical result reached by use of this invention is the obtaining of a bone biomaterial with maintained architectonics and pure bone collagen being low-antigenic materials, which can be widely used for obtaining products of medical purpose, such as materials for restoration of bone defects and also as a carrier of active substances and cells and which is able to be a base for other products of medical purpose.

As regards to the method, the mentioned technical result is reached in that the bone is sawn to plates with the thickness of 0.2 to 2.0 cm, washed with 0.1 M phosphate buffer, pH 5.8-6.0, heated to 65° C., digested in the solution of the activated 0.1-0.4% papain at 65° C. for 24 hours, then the plates are washed with 5 vol. parts of water at 40-80° C. (preferably 50-60° C.), treated with the 0.4 N alkali solution at room temperature for 10-24 hours, washed with flowing water, defatted in ethanol/chloroform mixtures in proportion of 1:2 and 2:1, decalcified in 0.4-1N hydrochloric acid, treated with 1.5-3% hydrogen peroxide for 4 hours, washed with treated water, then with ethanol at room temperature, and packed and sterilized.

As regards to the material, the technical result is reached in that the material for osteoplasty and tissue engineering obtained on the basis of this method represents a compound with the native spatial organization of the collagenic matrix and mineral component of the bone tissue of natural origin containing 25% of collagen and 75% of mineral substance. According to analysis results of the dry material, this material contains less than 1% of non-collagenic proteins.

A spongy or cortical bone of human or vertebrates, e.g., pigs, bucks, hens, geese etc. can serve as a material for obtaining the bone collagen and products on the basis of this. This tissue mainly consists of collagen of type I and III and is characterized by low solubility and also high resistance to collagenase. This type of the collagen is the most widely used in products for medical purposes being implanted into the organism tissues.

The attributes mentioned both for the method and for the material are essential and interconnected with forming a stable aggregate of essential attributes sufficient for obtaining the required technical result.

The technical essence of the method according to this invention and characteristics of the material for osteoplasty and tissue engineering obtained with use of this method are described below.

DETAILED DESCRIPTION OF THE INVENTION

The present invention is related to international application number PCT/RU2005/000526, filed on Oct. 27, 2005, which is incorporated herein by reference in its entirety.

The process of preparation of bioimplants applied according to this method requires an initial mechanical treatment of the tissue, when the bone is cleaned free from any remaining soft tissues and blood.

An essential attribute of the invention is the procedure of the bone treatment. After mechanical treatment the tissue is sawn up to form plates with a thickness not less than 0.2 cm and not more than 2.0 cm, as these dimensions are optimal by treatment of this tissue with solutions. The minimum size of plates with the minimum thickness 0.2 cm and minimum thickness 2.0 cm were determined by us experimentally. So, difficulties emerge with accessibility of enzyme and other solutions to active places of the substrate and also by washing of such plates free from solutions applied according to this technology by the increase of the plate thickness. Serious problems with maintaining continuity of the bone collagen and spatial structure of the bone tissue during the material treatment process arise by reduction of the plate thickness.

After cutting, the tissue is washed with the double volume of the 0.1 M phosphate buffer with pH 5.8-6.0 heated to 65° C. Namely washing in the phosphate buffer heated to 65° C. precedes digesting with the enzyme and creates optimal conditions for subsequent effect of the papain enzyme by sufficient reduction of incubating time with the enzyme by these pH values.

The enzyme is able to destroy non-collagenic proteins, proteoglycans and glycoproteins of the bone tissue effectively under these conditions, while fibers of the bone collagen are fully screened with a hydroxyapatite layer and so the bone collagen fibers are not exposed to denaturation and destruction maintaining their native structure by digesting in conditions of increases of temperature up to 65° C. This is clearly seen on the output of sulphated glycosaminoglycans and amino acids to digest.

Various concentration of the enzyme can be taken depending on the structure of the bone tissue and its thickness. So, the concentration of 0.1% activated papain is sufficient by the thickness of the spongy bone of 0.2 cm or, in case of treatment of the cortical bone, the papain concentration is increased to 0.4%.

The optimal effect of the papain onto the bone tissue by digesting of proteins and proteoglycans is 24 hours at 65° C. At that time, the maximum quantity of non-collagenic proteins and proteoglycans is removed from the bone tissue. It has been found by us experimentally that about 2 g of glycosaminoglycans is extracted to the digest from 1 kg of bones in 24 hours, which is practically equal to the theoretically calculated quantity of sGAG for this type of tissue (Chvapil M., Physiology of connective tissue, Butterworths, London, 1967, p. 67-70).

The bone plates are washed with 5 vol. parts of flowing water heated to 40-80° C. (preferably 50-60° C.) after their digesting with the enzyme. This operation allows for removal of all reaction products of the substrate with the enzyme, the enzyme itself and the major part of fats (more than 90%).

The effective defatting and removal of possibly remaining non-collagenic proteins is reached by the effect of the alkali onto the non-decalcified bone tissue. The treatment of the bone tissue with 0.4H NaOH (sodium hydroxide) is carried out for 10-24 hours at room temperature. It is well-known that this alkali is a very effective agent for destructing protein compounds, bacterial and viral particles, with which the bone tissue can be contaminated. This stage must be carried out at room temperature (18-20° C.), as the efficiency of such effects is significantly reduced by lower temperatures and the structure of the collagenic molecule itself and of the collagenic matrix can be destroyed by the temperature increase. As in the case with the enzyme, the initial mineral bone structure covering the collagenic matrix of the bone does not allow the 0.4H alkali solution to have an effect on the structure of the bone collagen even after its influence for 24 hours.

The spongy bone with the plates having sizes of 0.2 to 0.5 cm is treated for 10 hours, as protein molecules located on the surface of the collagen fibers are fully destroyed during this period of time. The thicker plates of the spongy bone and fragments of the cortical bone require the application of an alkali for 24 hours. The protein is not detected in the washouts from the tissue after this time.

After treatment with alkali, the bone is washed 5 times in flowing water and the plates are dried at room temperature.

As opposed to all known methods of obtaining biomaterials from the bone, this method proposes to carry out initial treatment of washing and enzymatic influence at high temperatures (65° C.), but then the destruction of the collagen molecule and collagenic matrix as a whole does not occur. In addition, it is proposed in this method to proceed with defatting and decalcification of the bone after its treatment with the enzyme and alkali only, as main antigens are already removed from the non-decalcified bone and the bone collagen remains practically unchanged due to a protective layer of hydroxyapatite covering the bone fiber.

A significant quantity of fats and their compounds with proteins and carbohydrates is contained in the bone tissue. The lipids are both in the free state and in form of compounds with sugars such as lipopolysaccharides, which are active antigens and can cause various inflammatory complications in the bone plates treated with the enzyme. The method includes the treatment of bone plates in mixtures of chloroform and ethanol in proportions of 2:1 and 1:2 at the stage, when the main bone stroma is already cleaned free from its other components, namely for removal of all remained lipids. The treatment in the mixture is carried out for 48 hours in each mixture until the complete removal of lipids, which can be estimated on the basis of the content of fats in 1 g of the dry tissue.

This stage ensures the liberation of lipids even from the dense bone tissue (cortical bone). After such treatment, their output is terminated and the content in the material does not exceed 1%. After defatting, the bone plates are dried and decalcified in solutions of mineral acids. As a rule, thin plates of the spongy bone are treated with a 0.4H solution of hydrochloric acid (HCl), and thicker plates (1 cm and more) in 1H HCl and the process is continued until the complete elimination of $Ca^{++}$ ions in the decalcifying solution. The decalcification process of the bone mineral cannot be conducted at all or the demineralization degree of the material can be strictly programmed.

The analytical study of the method for obtaining a material without demineralization has shown that the obtained material has classic indications of the bone tissue: 25% of collagen and 75% of mineral substance. At that, not only the structural collagen is not affected, but the spatial organization of the collagenic matrix and mineral component part of the bone tissue remains fully maintained. The obtained material differs from all materials at present applied in osteoplasty, both in its composition and operating characteristics and also in full absence of non-collagenic components and antigenic features. This material practically fully maintains the native spatial structure of the bone tissue, which is particularly necessary for good integration, biocompatibility and cellular colonization. Furthermore, this material undergoes treatment with 1.5-3% hydrogen peroxide for 4 hours.

This stage allows, first, the removal of remaining non-collagenic protein molecules, and second to destroy a series of other compounds such as pigments, remained lipids, not readily soluble salts, etc. 3% hydrogen peroxide is usually used for treatment of plates with a thickness of more than 1.0 cm. The obtained collagen is then washed 5 times in treated water, then in ethanol, dried at the room temperature, packed and sterilized.

The obtaining of the material is controlled at each processing stage and includes main methods accepted for these types of materials.

The absence of proteoglycans was determined on changes in coloration of the substrate and in the solutions spectrophotometrically in the presence of 1.9-dimethylene blue by the wavelength of 535 nm based on Farndel's method.

The protein output was determined based on Lowry's pharmacopeia method spectroscopically by the wavelength of 400 nm and the presence of collagen remainders in washouts with the use of Kjeldal's method for determination of oxyprolines.

The presence of calcium ions in decalcifying solutions was determined with the help of a qualitative reaction to $Ca^{2+}$. The control of lipids was carried out by painting the material with Sudan. The structural integrity of the bone collagen was determined by study of histologic sections, electron microscopically and with use of scanning microscopy method. It was established with the help of these methods that the porous-fibrous structure of the bone collagen has a typical appearance without any changes and abnormalities.

The control instrumentation was carried out after drying and sterilization for measurement of the content of non-collagenic proteins in the material as compared with the prototype. So, 4-5% of protein is determined per dry weight of the material obtained according to the method described in the prototype and less than 1% according to the method proposed in the present invention. Thus, the proposed method allows for a significant reduction of the material's antigenicity due to a more complete removal of non-collagenic proteins as compared with the prototype. Therefore, the proposed method of tissue treatment maintains the native structure of the material, improves its quality, reduces the material's and thereby ensures good plastic features, biointegration and biocompatibility.

Brief Description of a Process Used for Obtaining of Material

The pig's bone, passed through a required veterinary control, is cleaned of muscles and tendons, sawn up into plates with a thickness of 2.0 cm and put into a 0.1 M phosphate buffer at 65° C., pH 5.8-6.0. The buffer is poured off and the material is washed again with the heated buffer and transferred into a solution of activated 0.4% papain. The incubating is carried out at 65° C. in the thermostat for 24 hours. The digest is then poured off and the plates are washed with 5 volumes of water heated to 70° C., cooled to room temperature and put into a 0.4H alkali solution for 24 hours. The material is washed free from alkali, dried and treated twice, first with an ethanol/chloroform mixture in proportion of 1:2 for 48 hours and then with an ethanol/chloroform mixture in proportion of 2:1 for the subsequent 48 hours.

The bone plates are dried again and put into the 1 N hydrochloric acid. The change of acid is carried out until there is complete elimination of calcium ions in the decalcifying solution. The acid is washed with water and the plates are put into 3% hydrogen peroxide for 4 hours. Then the plates are washed with the treated water and ethanol, the material is dried, packed and sterilized.

These actions mentioned above lead to reduction of antigenicity and maintaining of the collagenic structure and bone collagenic matrix.

The quantitative and qualitative analysis of the bone collagen is conducted as described above.

The invention is explained by examples of specific executions for a better insight of the present invention.

Example 1

A donor human bone, passed through the required analyses, is mechanically cleaned of muscles and tendons, sawn up into plates with a thickness of 0.2-0.6 cm and put into a 0.1 M phosphate buffer at 65° C., pH 5.8-6.0, twice for 30 minutes each time. The buffer is then poured off and the plates are transferred into a solution of activated 0.15% papain at 65° C. into the thermostat for 24 hours. Then the supernatant is poured off, the plates are washed with 5 volumes of water at 60° C., cooled to room temperature and put into the 0.4H alkali solution for 24 hours. The material is washed free from alkali and dried. The plates are put first into an ethanol/chloroform mixture in proportion of 1:2 twice for 4 hours and then twice into the same mixture but in proportion of 2:1 for 24 hours.

The material is dried and treated with the 1.5% hydrogen peroxide for 4 hours. Then the plates are washed first with the treated water and then with ethanol. For obtaining a bone collagen, the material is dried after its defatting in organic solutions and decalcified in 0.5 N hydrochloric acid. The acid is washed out and the bone plates are treated with the 1.5% hydrogen peroxide for 4 hours. Then the material is washed again first with the treated water and then with ethanol. The material treated by the use of such method is dried at room temperature, frozen-dried, packed and sterilized by use of a radiation method. Bones of animals with a thickness of up to 0.8 cm are treated in a similar manner.

The analytic study with respect to the presence of proteins, proteoglycans and lipids in the material is conducted at the end of each technological cycle. The obtained materials are applied for restoration of bone defects by operative intervention in stomatology, orthopedics and traumatology. The non-decalcified bone material and bone collagen can be saturated with bioactive substances (sulfated glycosaminoglycans, growth factors such as PDGF, IGF, FGF etc.) for clinical, experimental and scientific purposes and also can be used as carriers for various types of cells such as stem cells, embryonic cells, blood cells etc.

Example 2

The pig's spongy bone, passed through a required veterinary control, is mechanically cleaned of muscles and tendons, sawn up into plates with a thickness of 1.1-2.0 cm and put into a 0.1 M phosphate buffer at 65° C., pH 5.8-6.0, twice for 60 minutes each time. The buffer is then poured off and the plates are transferred into a solution of activated 0.3% papain at 65° C. into the thermostat for 24 hours. Then the digest is poured off, the plates are washed with 5 volumes of water at 70° C., cooled and put into the 0.4H alkali solution at room temperature for 24 hours. The material is washed free from alkali and dried.

The plates are put first into an ethanol/chloroform mixture in proportion of 1:2 twice for 4 hours and 24 hours and then twice into the same mixture but in proportion of 2:1 for the subsequent 4 hours and 24 hours. After defatting, the material is dried and treated immediately with an 3.0% hydrogen peroxide for 4 hours or decalcified in the 1 N hydrochloric acid and then treated with the 3.0% hydrogen peroxide for 4 hours with the following washing free from the acid. Both kinds of material are washed first with the treated water and then with ethanol.

The bone matrix and bone collagen obtained in such a way are cut into fragments of various shape and size: cubes, parallelepipeds, blocks etc. and dried at room temperature or by use of a lipophilic method, packed and sterilized by radiation. Bones of various animals and humans with a thickness exceeding 1 cm are treated in a similar manner.

The analytical study with respect to the presence of proteins, proteoglycans and lipids in the material is conducted at the end of each technological cycle. The obtained materials are applied for restoration of bone defects by operative intervention in stomatology, orthopedics and traumatology. The non-decalcified bone material and bone collagen can be saturated with bioactive substances (sulfated glycosaminoglycans, growth factors such as PDGF, IGF, FGF etc.) for clinical, experimental and scientific purposes and also can be used as carriers for various types of cells such as stem cells, embryonic cells etc.

Example 3

The pig's cortical bone, passed through a required veterinary control, is mechanically cleaned of muscles and tendons, sawn up into plates with a thickness of 1.5-2.0 cm and put into a 0.1 M phosphate buffer at 65° C., pH 5.8-6.0, twice for 60 minutes each time. The buffer is then poured off and the plates are transferred into a solution of activated 0.4% papain at 65° C. into the thermostat for 24 hours. Then the digest is poured off, the plates are washed with 5 volumes of water at 80° C., cooled and put into a 0.4 N alkali solution at room temperature for 24 hours.

The material is washed free from alkali and dried. The plates are put first into an ethanol/chloroform mixture in proportion of 1:2 twice for 4 hours and 24 hours and then twice into the same mixture but in proportion of 2:1 for the subsequent 4 hours and 24 hours. As in the previous example, the material is dried and treated immediately with the 3.0% hydrogen peroxide for 24 hours (osteomatrix) or decalcified in the 1 N hydrochloric acid and only then treated with the 3.0% hydrogen peroxide for 24 hours after washing free from the acid (bone collagen). Both kinds of material are washed first with the treated water and then with ethanol.

The biomaterials obtained by such a way are cut into fragments of various shape and size: cubes, parallelepipeds, disks, blocks etc. and dried at the room temperature, packed and sterilized by radiation. Bones of various animals and humans with a thickness exceeding 1 cm are treated in a similar manner. The analytical study with respect to the presence of proteins, proteoglycans and lipids in the material is conducted at the end of each technological cycle.

The obtained materials are applied for restoration of bone defects by operative intervention in stomatology, orthopedics and traumatology. The non-decalcified bone material and bone collagen can be saturated with bioactive substances (sulfated glycosaminoglycans, growth factors such as PDGF, IGF, FGF etc.) for clinical, experimental and scientific purposes and also can be used as carriers for various types of cells such as stem cells, embryonic cells etc.

Example 4

A donor human bone, passed through the required analyses, is mechanically cleaned of muscles and tendons, sawn up into plates with a thickness of 0.5-0.8 cm and is treated as per example 1 until the decalcification stage. Then defatted bone plates are dried and treated with the 1.5% hydrogen peroxide for 6 hours. The plates are washed first with the treated water and then with ethanol. The material treated in such a way is dried at room temperature, frozen-dried, packed and sterilized by radiation. Bones of animals with the thickness of 0.5 to 1.0 cm are treated in a similar manner.

The analytical study with respect to the presence of proteins, proteoglycans and lipids in the material is conducted at the end of each technological cycle.

Example 5

The pig's spongy or cortical bone, passed through a required veterinary control, is mechanically cleaned of muscles and tendons, sawn up into plates with a thickness of 1.0-2.0 cm and then treated as per example 2 until the decalcification stage. Then defatted bone plates are dried and treated with the 1.5% hydrogen peroxide for 6 hours. The plates are washed first with the treated water and then with ethanol. The material treated by such a way is dried at the room temperature, frozen-dried, packed and sterilized ethanol. Bones of animals with a thickness of 0.5 to 1.0 cm are treated in a similar manner.

INDUSTRIAL APPLICABILITY

This invention is industrially applicable, mastered in vitro, such that the laboratory results show the practical value of the obtained material for osteoplasty and tissue engineering.

What is claimed is:

1. A method for obtaining bone plates, from tissue of a bone, the method comprising:
    (a) cleaning the bone;
    (b) sawing the bone into plates having a thickness of 0.2-2.0 cm;
    (c) washing the plates twice in a 0.1 M phosphate buffer solution having a pH of 5.8-6.0 and a temperature of 65° C., wherein the ratio of bone plates to buffer solution is 1:2 by volume;
    (d) immersing the plates in a 0.1-0.4% solution of activated papain at 65° C. for 24 hours;
    (e) washing the plates five times with water having a temperature 40-80° C.;
    (f) treating the plates with 0.4 N alkali solution at room temperature for 10-24 hours;
    (g) washing the plates with water;
    (h) drying the plates;
    (i) removing fat from the plates by washing with an ethanol and chloroform mixture, wherein the ratio of ethanol to chloroform is 2:1 by volume;
    (j) removing fat from the plates by washing with an ethanol and chloroform mixture, wherein the ratio of ethanol to chloroform is 1:2 by volume;
    (k) decalcifying the plates with a solution of hydrochloric acid;
    (l) treating the plates with a solution of hydrogen peroxide for 4 hours;
    (m) washing the plates with water at room temperature until the hydrogen peroxide is removed from the plates;
    (n) washing the plates with ethanol;
    (o) drying the plates;
    (p) packing the plates; and
    (q) sterilizing the plates.

2. A method for obtaining bone fragments from tissue of a bone, the method comprising:
    (a) sawing the bone into fragments having a thickness of 0.2-2.0 cm;
    (b) washing the fragments in a 0.1 M phosphate buffer solution having a pH of 5.8-6.0 and a temperature of 65° C.;
    (c) immersing the fragments in a solution of activated papain;
    (d) washing the fragments with water;
    (e) treating the fragments with a 0.4 N alkali solution at room temperature;
    (f) washing the fragments with water;
    (g) drying the fragments;
    (h) removing fat from the fragments by washing with an ethanol/chloroform mixture;
    (i) decalcifying the fragments with a solution of an acid;
    (j) treating the fragments with hydrogen peroxide;
    (k) washing the fragments with water until the hydrogen peroxide is removed from the fragments;
    (l) washing the fragments with ethanol; and
    (m) drying the fragments.

3. The method of claim 1, wherein the drying in step (g) includes freeze-drying.

4. The method of claim 1, wherein the papain solution is 0.1-0.4% papain.

5. The method of claim 1, wherein the papain solution is at 65° C.

6. The method of claim 1, wherein the immersing step lasts for about 24 hours.

7. The method of claim 1, wherein step (d) is performed multiple times.

8. The method of claim 1, wherein the water in step (d) has a temperature of 40-80° C.

9. The method of claim 1, wherein step (e) is performed for 10-24 hours.

10. The method of claim 1, wherein the ethanol and chloroform mixture of step (h) has a 2:1 ratio by volume of ethanol to chloroform.

11. The method of claim 10, wherein in step (h) the bone fragments are further washed with an ethanol and chloroform mixture having a 1:2 ratio by volume of ethanol to chloroform.

12. The method of claim 1, wherein the acid in step (i) is hydrochloric acid.

13. The method of claim 12, wherein the hydrochloric acid concentration is 0.4-1.0 N.

14. The method of claim 1, wherein step (j) is performed for 4 hours.

15. The method of claim 1, wherein the water in step (k) is at room temperature.

16. The method of claim 1, further comprising the steps of:
    (n) packing the fragments; and
    (o) sterilizing the fragments.

17. The method of claim 1, wherein the fragments are any of plates, cubes, parallelepipeds and blocks.

18. The method of claim 1, further comprising cleaning the bone prior to step (a).

19. The method of claim 1, wherein in step (b) the ratio of bone fragments to buffer solution is 1:2 by volume.

* * * * *